(12) United States Patent
Pravetoni

(10) Patent No.: US 12,070,492 B2
(45) Date of Patent: Aug. 27, 2024

(54) THERAPEUTIC COMPOSITIONS AND METHODS WITH CYTOKINE SIGNALING IMMUNOMODULATORS

(71) Applicant: Hennepin Healthcare Research Institute, Minneapolis, MN (US)

(72) Inventor: Marco Pravetoni, Minneapolis, MN (US)

(73) Assignee: Hennepin Healthcare Research Institute, Minneapolis, MN (US)

( * ) Notice: Subject to any disclaimer, the term of this patent is extended or adjusted under 35 U.S.C. 154(b) by 628 days.

(21) Appl. No.: 16/099,093

(22) PCT Filed: May 10, 2017

(86) PCT No.: PCT/US2017/031907
§ 371 (c)(1),
(2) Date: Nov. 5, 2018

(87) PCT Pub. No.: WO2017/196943
PCT Pub. Date: Nov. 16, 2017

(65) Prior Publication Data
US 2019/0125851 A1 May 2, 2019

Related U.S. Application Data

(60) Provisional application No. 62/334,167, filed on May 10, 2016.

(51) Int. Cl.
| | |
|---|---|
| A61K 39/00 | (2006.01) |
| A61K 31/485 | (2006.01) |
| A61K 38/20 | (2006.01) |
| A61K 39/385 | (2006.01) |
| A61K 39/39 | (2006.01) |
| A61K 39/395 | (2006.01) |
| A61K 47/64 | (2017.01) |
| A61P 25/30 | (2006.01) |
| A61P 25/36 | (2006.01) |
| C07K 16/24 | (2006.01) |
| C07K 16/28 | (2006.01) |

(52) U.S. Cl.
CPC ........ A61K 39/0018 (2013.01); A61K 31/485 (2013.01); A61K 38/20 (2013.01); A61K 39/385 (2013.01); A61K 39/39 (2013.01); A61K 39/39541 (2013.01); A61K 39/3955 (2013.01); A61K 39/39583 (2013.01); A61K 47/643 (2017.08); A61P 25/30 (2018.01); A61P 25/36 (2018.01); C07K 16/247 (2013.01); C07K 16/248 (2013.01); C07K 16/2866 (2013.01); A61K 2039/505 (2013.01); A61K 2039/555 (2013.01); A61K 2039/55505 (2013.01); A61K 2039/6012 (2013.01); A61K 2039/6081 (2013.01)

(58) Field of Classification Search
None
See application file for complete search history.

(56) References Cited

U.S. PATENT DOCUMENTS

| | | | |
|---|---|---|---|
| 5,747,024 A | 5/1998 | Grabstein et al. | |
| 5,914,110 A | 6/1999 | Holmes et al. | |
| 6,488,936 B1 | 12/2002 | Mishkin et al. | |
| 6,838,081 B1 | 1/2005 | Roth et al. | |
| 9,308,280 B2 | 4/2016 | Shi et al. | |
| 10,314,904 B2* | 6/2019 | Purcell .................. | C07K 16/28 |
| 2003/0211104 A1 | 11/2003 | Furfine et al. | |
| 2010/0254993 A1 | 10/2010 | Carballido Herrera et al. | |
| 2014/0093525 A1* | 4/2014 | Pentel .................. | A61K 39/385 |
| | | | 424/185.1 |

FOREIGN PATENT DOCUMENTS

WO    WO 2015/035010 A1    3/2015

OTHER PUBLICATIONS

Tang, Y. W., and Graham, B. S. Anti-IL-4 treatment at immunization modulates cytokine expression, reduces illness, and increases cytotoxic T lymphocyte activity in mice challenged with respiratory syncytial virus. The Journal of Clinical Investigation, 94(5) pp. 1953-1958, 1994 (Year: 1994).*
The European Medicines Agency, Evaluation of Medicines for Human Use, Guideline on Adjuvants in Vaccines, 18 Pages, Jan. 20, 2005 (Year: 2005).*
Jackson et al. Novel HIV IL-4R antagonist vaccine strategy can induce both high avidity CD8 T and B cell immunity with greater protective efficacy. Vaccine. Sep. 29, 2014;32(43):5703-14.*
Alving et al. Adjuvants for vaccines to drugs of abuse and addiction. Vaccine. Sep. 22, 2014;32(42):5382-9.*
McKee et al., Alum induces innate immune responses through macrophage and mast cell sensors, but these sensors are not required for alum to act as an adjuvant for specific immunity. J Immunol 183, 4403-4414 (2009). (NIH-PA Author Manuscript version provided, 28 pages.).
Laudenbach et al., Blocking interleukin-4 enhances efficacy of vaccines for treatment of opioid abuse and prevention of opioid overdose. Sci Rep 8, 5508 (2018), 12 pages.

(Continued)

*Primary Examiner* — Dong Jiang
(74) *Attorney, Agent, or Firm* — MUETING RAASCH GROUP

(57) ABSTRACT

A method generally includes co-administering to a subject a composition that includes an antigen and a cytokine signaling immunomodulator. The method can be for treating a subject for abuse of a drug, treating a subject for toxicity from drug abuse, treating a subject for infection by a pathogen, treating a subject for a non-communicable disease, or for increasing antibody production against the antigen. The antigen can be component of a vaccine. The cytokine-signaling immunomodulator is effective to improve the subject's immune response to the antigen compared to the subject's immune response to the antigen without the cytokine-signaling immunomodulator.

6 Claims, 11 Drawing Sheets

(56) References Cited

OTHER PUBLICATIONS

Goniewicz et al., Nicotine vaccines to treat tobacco dependence. Hum Vaccin Immunother 9, 13-25 (2013).
Castro et al., Anti-interleukin 10 receptor monoclonal antibody is an adjuvant for T helper cell type 1 responses to soluble antigen only in the presence of lipopolysaccharide. J Exp Med 192, 1529-1534 (2000).
European Patent Application No. 17796740.3, filed Dec. 3, 2018, Extended European Search Report issued Jun. 25, 2020, 12 pages.
International Patent Application No. PCT/US2017/031907, filed May 10, 2017; International Preliminary Report on Patentability issued Nov. 13, 2018; 9 pages.
International Patent Application No. PCT/US2017/031907, filed May 10, 2017; International Search Report and Written Opinion, issued Aug. 22, 2017; 12 pages.
Boyman, et al., "Selective Stimulation of T Cell Subsets with Antibody-Cytokine Immune Complexes", Mar. 31, 2006, *Science*, 311:1924-1927.
Chow, et al., "Development of Th1 and Th2 Populations and the Nature of Immune Responses to Hepatitis B Virus DNA Vaccines Can be Modulated by Codelivery of Various Cytokine Genes", 1998, *J Immunol*, 160:1320-1329.
Finkelman, et al., "Anti-Cytokine Antibodies as Carrier Proteins. Prolongation of in Vivo Effects of Exogenous Cytokines by Injection of Cytokine-Anti-Cytokine Antibody Complexes.", Aug. 1, 1993, *J Immunol*, 151(3):1235-1244.
Kayamuro, et al., "Interleukin-1 Family Cytokines as Mucosal Vaccine Adjuvants for Induction of Protective Immunity against Influenza Virus$^\nabla$", Dec. 2010, *Journal of Virology*, 84(24):12703-12712. Published ahead of print on Sep. 29, 2010.
Laudenbach et al., "The Frequency of Naive and Early-Activated Hapten-Specific B Cell Subsets Dictates the Efficacy of a Therapeutic Vaccine against Prescription Opiod Abuse", 2015, *J Immunol* 194(12):5926-5936. Available online May 13, 2015.
Mostböck, et al., "IL-2/Anti-IL-2 Antibody Complex Enhances Vaccine-Mediated Antigen-Specific CD8$^+$T Cell Responses and Increases the Ratio of Effector/Memory CD8$^+$T Cells to Regulatory T Cells[1]", 2008, *The Journal of Immunology*, 180:5118-5129.
Orson, et al., "The future potential for cocaine vaccines", Sep. 4, 2014, *Expert Opin Biol Ther*, 14(9):1271-1283.
Phelan, et al., "Cutting Edge: Mechanism of Enhancement of In Vivo Cytokine Effects by Anti-Cytokine Monoclonal Antibodies", 2008, *J Immunol*, 180:44-48.
Sundberg, et al., "Small-molecule control of cytokine function: new opportunities for treating immune disorders", 2014, *Current Opinion in Chemical Biology*, 23:23-30. Available online Sep. 15, 2014.
Tubo et al., "Single Naive CD4$^+$T Cells from a Diverse Repertoire Produce Different Effector Cell Types during Infection", May 9, 2013, *Cell* 153(4):785-796.
Verdeil, "Adjuvants targeting innate and adaptive immunity synergize to enhance tumor immunotherapy", Oct. 28, 2008, *PNAS*, 105(43):16683-16688.
Wack, et al., "Combination adjuvants for the induction of potent, long-lasting antibody and T-cell responses to influenza vaccine in mice", 2008, *Vaccine*, 26:552-561. Available online Dec. 26, 2007.
Wang, et al., "Selection of Adjuvants for Enhanced Vaccine Potency", 2011, *World Journal of Vaccines*, 1:33-78. Published online May 2011.
Yamazaki, et al., "Mucosal T Cells Expressing High Levels of IL-7 Receptor are Potential Targets for Treatment of Chronic Colitis[1]", 2003, *J Immunol*, 171:1556-1563.
Baruffaldi, et al., "Preclinical Efficacy and Characterization of Candidate Vaccines for Treatment of Opioid Use Disorders Using Clinically Viable Carrier Proteins," Nov. 5, 2018, Mol Pharm, 15(11):4947-4962. Author manuscript available Feb. 4, 2019.
Crouse, et al., "Mechanisms of interleukin 4 mediated increase in efficacy of vaccines against opioid use disorders," npj Vaccines (2020) 5:99, 13 pages.
Huseby Kelcher, et al., "Contribution of Antibody-Mediated Effector Functions to the Mechanism of Efficacy of Vaccines for Opioid Use Disorders," J Immunol 2021; 207:860-867. Prepublished online Jul. 19, 2021.
Laudenbach, et al., "The Frequency of Naive and Early-Activated Hapten-Specific B Cell Subsets Dictates the Efficacy of a Therapeutic Vaccine against Prescription Opioid Abuse," 2015 The Journal of Immunology, 194:5926-5936. Prepublished online May 13, 2015.
Chen et al. "High immunogenicity of nicotine vaccines obtained by intradermal delivery with safe adjuvants" Oct. 30, 2012, *Vaccine*, vol. 31, pp. 159-164.
DeVilliers et al. "Increased efficacy of a trivalent nicotine vaccine compared to a dose-matched monovalent vaccine when formulated with alum" Oct. 29, 2013, *Vaccine*, vol. 31, pp. 6185-6193.
Hanson et al. "Nanoparticulate STING agonists are potent lymph node-targeted vaccine adjuvants" Jun. 2015, *The Journal of Clinical Investigation*, vol. 125, No. 6, pp. 2532-2546.
Hwang et al. "Enhancing Efficacy and Stability of an Antiheroin Vaccine: Examination of Antinociception, Opioid Binding Profile, and Lethality" Mar. 5, 2018, *Mol. Pharm.*, vol. 15, No. 3, pp. 1062-1072.
Lockner et al. "Flagellin as Carrier and Adjuvant in Cocaine Vaccine Development" 2015, *Molecular Pharmaceutics*, vol. 12, pp. 653-662.
Matyas et al. "Liposomes Containing Monophosphoryl Lipid A: A Potent Adjuvant System for Inducing Antibodies to Heroin Hapten Analogs" Jun. 10, 2013, *Vaccine*, vol. 31, No. 26, pp. 2804-2810.
Pravetoni et al. "Co-administration of morphine and oxycodone vaccines reduces the distribution of 6-monoacetylmorphine and oxycodone to brain in rats" 2012, *Vaccine*, vol. 30, pp. 4617-4624.
Pravetoni et al. "Effect of Currently Approved Carriers and Adjuvants on the Pre-Clinical Efficacy of a Conjugate Vaccine against Oxycodone in Mice and Rates" May 2014, *PLOS One*, vol. 9, No. 5, 10 pages.
Pravetoni, "Biologics to treat substance use disorders: Current status and new directions" 2016, *Human Vaccines & Immunotherapeutics*, vol. 12, No. 12, pp. 3005-3019.
Pravetoni et al. "Formulation and Characterization of Conjugate Vaccines to Reduce Opioid Use Disorders Suitable for Pharmaceutical Manufacturing and Clinical Evaluation" 2019, *Molecular Pharmaceutics*, vol. 16, pp. 2364-2375.
Robinson et al. "Alum adjuvant is more effective than MF59 at prompting early germinal center formation in response to peptide-protein conjugates and enhancing efficacy of a vaccine against opioid use disorders" 2019, *Human Vaccines & Immunotherapeutics*, vol. 15, No. 4, pp. 909-917.
Robinson et al. "Therapeutic and Prophylactic Vaccines to Counteract Fentanyl Use Disorders and Toxicity" Jul. 13, 2020, *Journal of Medicinal Chemistry*, 21 pages.
Spinner et al. "Methylglycol chitosan and a synthetic TLR4 agonist enhance immune responses to influenza vaccine administered sublingually" Oct. 26, 2015, Vaccine, vol. 33, No. 43, pp. 5845-5853.
Zhao et al. "Rational incorporation of molecular adjuvants into a hybrid nanoparticle-based nicotine vaccine for immunotherapy against nicotine addiction" Feb. 2018, *Biomaterials*, vol. 155, pp. 165-175.
EP Patent Application No. 17 796 740.3, filed Dec. 3, 2018; Office Action issued Mar. 14, 2023.

* cited by examiner

THERAPEUTIC COMPOSITIONS AND METHODS WITH CYTOKINE SIGNALING IMMUNOMODULATORS

CROSS-REFERENCE TO RELATED APPLICATION

This application is the § 371 U.S. National Stage of International Application No. PCT/US2017/031907, filed 10 May 2017, which claims the benefit of U.S. Provisional Patent Application No. 62/334,167, filed May 10, 2016, each of which is incorporated herein by reference in its entirety.

GOVERNMENT FUNDING

This invention was made with government support under DA041730 awarded by the National Institutes of Health. The government has certain rights in the invention.

SUMMARY

This disclosure describes, in one aspect, a method for treating a subject for abuse of a drug or toxicity from drug abuse. Generally, the method includes co-administering to the subject a vaccine and a cytokine signaling immunomodulator. The vaccine generally includes a derivative of the drug conjugated to a carrier polypeptide in an amount effective to induce production of antibody that specifically binds to the drug. The cytokine-signaling immunomodulator is effective to improve the subject's immune response to the vaccine compared to the subject's immune response to the vaccine without the cytokine-signaling immunomodulator.

In some embodiments, the cytokine-signaling immunomodulator can be a complex that includes a cytokine and a monoclonal antibody that binds to the cytokine. In some of these embodiments, the complex can include an IL-4:anti-IL-4 monoclonal antibody complex, an IL-6:anti-IL-6 monoclonal antibody complex, or an IL-21:anti-IL-21 monoclonal antibody complex.

In some embodiments, the cytokine-signaling immunomodulator includes a monoclonal antibody that binds to IL-4, IL-6, IL-21, or other interleukin.

In some embodiments, the cytokine-signaling immunomodulator includes an antibody that specifically binds to the IL-7 receptor a chain (anti-CD127).

In some embodiments, the cytokine-signaling immunomodulator includes an interleukin.

In some embodiments, improvement of the subject's immune response to the vaccine includes an increase in antigen-specific IgG antibody level, an increase in antigen-specific IgG antibody concentration, or an increase in antigen-specific IgG antibody titer compared to the subject's immune response to the vaccine without the cytokine-signaling immunomodulator. In some embodiments, improvement of the subject's immune response to the vaccine includes increased production of $IgG_{2a}$ antibody subclass compared to the subject's immune response to the vaccine without the cytokine-signaling immunomodulator.

In some embodiments, improvement of the subject's immune response to the vaccine includes increased vaccine efficacy compared to the subject's immune response to the vaccine without the cytokine-signaling immunomodulator.

In some embodiments, improvement of the subject's immune response to the vaccine includes an increase in the percentage of vaccine responders compared to the subject's immune response to the vaccine without the cytokine-signaling immunomodulator.

In some embodiments, improvement of the subject's immune response to the vaccine includes at least partial reprogramming of an adaptive immune response in response to an antigen.

In another aspect, this disclosure describes a method for treating a subject for an infectious disease or for a non-communicable disease. Generally, the method includes co-administering to the subject a vaccine and a cytokine signaling immunomodulator. The vaccine generally includes a disease-specific immunogen in an amount effective to induce production of antibody that specifically binds to the immunogen. The cytokine-signaling immunomodulator is effective to improve the subject's immune response to the vaccine compared to the subject's immune response to the vaccine without the cytokine-signaling immunomodulator.

In some embodiments, improvement of the subject's immune response includes an increase in antigen-specific antibody production compared to the subject's immune response to the vaccine without the cytokine-signaling immunomodulator.

In some embodiments, improvement of the subject's immune response includes a subclass shift of antibody from $IgG_1$ to $IgG_2$ compared to the subject's immune response to the vaccine without the cytokine-signaling immunomodulator.

In another aspect, this disclosure describes a method for producing antibody against an antigen. Generally, the method includes administering to an animal a composition that includes the antigen and a cytokine-signaling immunomodulator effective to improve the animal's immune response to the antigen compared to the animal's immune response to the antigen without the cytokine-signaling immunomodulator.

In some embodiments, improvement of the animal's immune response includes an increase in antigen-specific antibody production compared to the animal's immune response to the antigen without the cytokine-signaling immunomodulator.

In some embodiments, improvement of the animal's immune response includes a subclass shift of antibody from $IgG_1$ to $IgG_2$ compared to the animal's immune response to the antigen without the cytokine-signaling immunomodulator.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
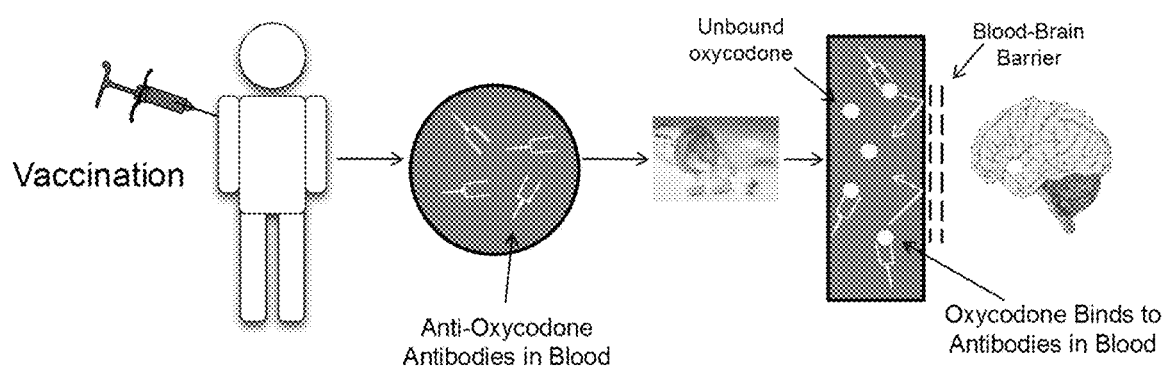
FIG. 1. A schematic illustrating the strategy of immunotherapy for treating drug abuse, dependence, relapse, toxicity, or overdose. In an unvaccinated individual, a drug of abuse (e.g., oxycodone, as shown) does not induce an immune response, due to its small molecular weight. The free drug crosses through the blood-brain barrier and binds to opioid receptors in the brain, causing changes in neuron signaling and brain neurochemistry. Vaccination stimulates production of antibodies against the drug. The antibodies bind to the drug and prevent it from crossing the blood-brain barrier, reducing drug-induced behavioral effects.
Figure 2:
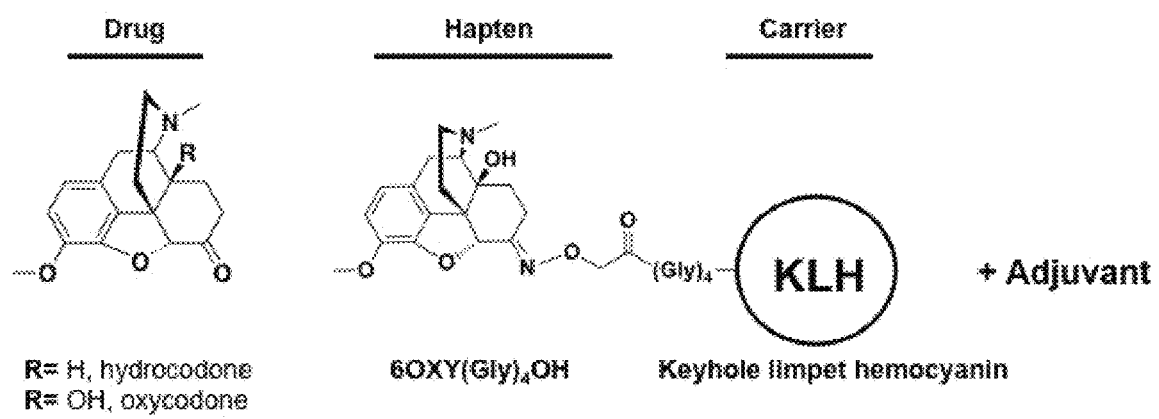
FIG. 2. The prescription opioids oxycodone and hydrocodone and a structurally-derived hapten. A tetraglycine linker was placed at the C6 position on the morphinan structure, and the oxycodone-based hapten (OXY) was conjugated through carbodiimide coupling chemistry to a carrier polypeptide. Other conjugation chemistries known to those skilled in the art can also be used. In this example, the OXY hapten was conjugated to the keyhole limpet hemocyanin (KLH) carrier polypeptide. The OXY and other opioid-based haptens have been conjugated to BSA, OVA, $CRM_{197}$, TT carrier polypeptides and TT-based peptides. Haptens can be conjugated to other carriers including peptides, polypeptides, but also to biomaterials (e.g., liposomes), and synthetic carriers of various composition (e.g., nanoparticles). The hapten-carrier conjugate is administered in combination with adjuvants (e.g., alum, MPLA, or MF59), but also with other delivery platforms (e.g., gels).
Figure 3:
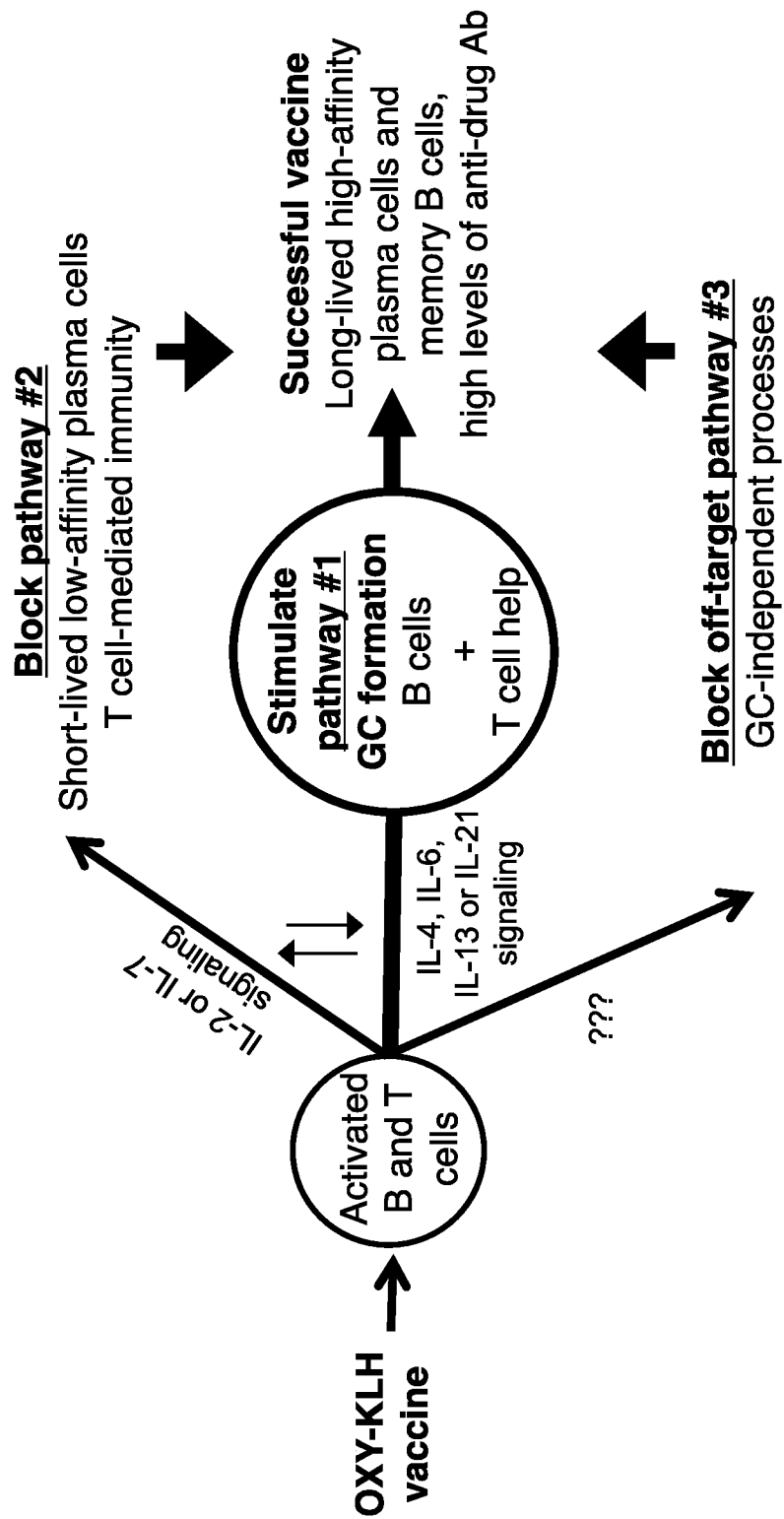
FIG. 3. Co-administration of cytokine signaling immunomodulators (e.g., interleukins, mAb for interleukins or interleukin receptors, or small molecules targeting interleukin signaling) can enhance T cell-dependent B cell activation and formation of germinal centers (GC) in secondary lymphoid organs and vaccine efficacy. IL-4, IL-6, IL-13, and IL-21 promote either GC formation, isotype class switching, affinity maturation, and/or up-regulate other key pathways associated with activation of GC B cells and T follicular helper (Tfh) cells (FIG. 3, pathway #1). In contrast, IL-2 and IL-7 inhibit GC formation (FIG. 3, pathway #2) by controlling $CD4^+$ T cell differentiation, and limiting formation of Tfh cells. Other less characterized signaling pathways contribute to off-target processes, which distract the adaptive immune system from GC formation (FIG. 3, pathway #3).

Vaccines may offer a therapeutic option for treating drug abuse and dependence, relapse to drug use after a period of abstinence, and drug-related toxicity such as overdose death. A small molecule drug such as, for example, an opioid (e.g., heroin or a prescription opioid) or a stimulant (e.g., nicotine, cocaine, amphetamine, methamphetamine), can be made immunogenic by conjugating the small molecule to a larger, foreign carrier polypeptide or other immunogenic structure (e.g., nanoparticle or liposome) to elicit serum antibodies that bind drug in serum, prevent its distribution to the brain, and subsequently reduce the likelihood or extent of drug-induced behavior or drug-induced toxicity. However, eliciting high levels of drug-specific serum antibodies has remained a challenge in translating these vaccines to human use.

Clinical efficacy of therapeutic vaccines for substance use disorder depends, at least in part, on achieving high levels of effective high affinity anti-drug antibodies. Antibodies are generated as a result of T cell-dependent B cell activation in germinal centers (GC) of secondary lymphoid organs where antigen-specific GC B cells, aided by T follicular helper ($T_{fh}$) cells, differentiate into long-lived antibody-secreting B cells (ASC) and switched immunoglobulin (swIg) memory B cells. The formation of germinal centers is a complex process modulated by interleukins, co-stimulatory molecules, and by downstream signaling pathways in antigen-specific B and T cells.

Pre-clinical and clinical efficacy of vaccines for substance use disorders is achieved in the subset of immunized subjects (~30%) showing high levels of anti-drug antibodies that block drug distribution to the brain and rewarding effects. Drug-based haptens conjugated to a carrier polypeptide can stimulate T cell-dependent B cell differentiation in germinal centers (GC). Post-immunization anti-drug antibody levels, anti-drug antibody efficacy in limiting drug distribution in the brain, and anti-drug antibody efficacy reducing drug-induced behavior in mice increase with an increased frequency of naïve and early-activated hapten-specific B cells, increased frequency of carrier-specific CD4+ T cells, and the magnitude of GC activation. After immunization, commitment of naïve B cells and T cells to germinal center formation, or GC-independent pathways, is regulated by cytokines and co-stimulatory molecules. Interleukin (IL) receptors activate JAK/STAT signaling, while specific STAT proteins activate transcription programs leading to B cell and T cell differentiation in germinal center B cells and $T_{FH}$ cells. The effects of interleukins on expression of STAT proteins, and activity of bcl-6 or blimp-1, have been characterized in $T_{FH}$ cells. In contrast, less is known of the role of these pathways in germinal center B cells and their contribution to antibody generation. For instance, IL-4 and IL-21 promote germinal center formation, isotype class switching, and affinity maturation. In contrast, IL-2 and IL-7 inhibit germinal center formation by controlling CD4+ T cell differentiation, and limiting formation of $T_{FH}$ cells. IL-2 receptor (IL-2R) activates STAT5, which activates blimp-1, resulting in formation of short-lived antibody-secreting B cells and $Th_1$ cell-based immunity.

This disclosure describes technology that involves programming T cell-dependent B cell differentiation toward GC formation by modulating cytokine signaling to increase the efficacy of vaccines for substance use disorders. Moreover, the combination of conjugate vaccines with cytokine signaling modulators had a synergistic effect (i.e., vaccine plus immunomodulator was better than vaccine alone), and this result was unexpected. Immunomodulators (e.g., IL-2, IL-2:anti-IL-2 mAb complexes, or IL-4:anti-IL-4 mAb complexes) have been previously used alone (e.g., IL-2 cancer therapy) or combined with immunogens and shown increased cellular immunity (e.g., CD8+ T cells) or innate immunity (e.g., macrophages). In contrast, this disclosure describes combining such immunomodulators with vaccines, thereby improving the humoral response (e.g., antigen-specific CD4+ $T_{FH}$ cells and B cells, antigen-specific antibodies). Hence, the technology described herein is effective to reprogram the adaptive immune response toward an increased humoral response against the target drug.

For example, a model vaccine against the highly abused prescription opioid oxycodone was combined with IL-4, IL-6, IL-21, anti-IL-4 mAb, or an IL-4:anti-IL-4 mAb complex to promote germinal center formation, or with a mAb against the IL-2 receptor alpha chain (IL-2αR or CD25) to block IL-2-mediated inhibition of germinal center formation. The IL-4:anti-IL-4 mAb complexes and the anti-IL-4 mAb enhanced post-immunization anti-oxycodone polyclonal antibody levels, vaccine efficacy in blocking oxycodone distribution to the brain, and the percentage of subjects showing vaccine efficacy. Specifically, blocking IL-4 with an anti-IL-4 mAb increased vaccine efficacy by inducing $IgG_{2a}$ and $IgG_3$ antibody subclasses, suggesting that $IgG_{2a}$-mediated effector functions and/or $IgG_3$-mediated effector functions, such as macrophage active removal of the target antigen, are involved. Manipulating IL-4 signaling also elicited greater post-immunization hapten-specific GC B cells and carrier-specific $T_{fh}$ cells, but did not alter GC-independent B and T cell differentiation. For instance, blocking IL-4 with an anti-IL-4 mAb increased GC formation in response to a peptide-protein conjugate immunogen, suggesting that this approach may be extended to other vaccines. In fact, co-administration of an anti-IL-4 mAb with a tetanus-diphtheria-pertussis vaccine increased tetanus-specific antibodies, enhanced the tetanus-specific $IgG_{2a}$ response, and resulted in greater efficacy against diphtheria. These data were supported by evidence that the immunogenicity and the efficacy of an oxycodone vaccine was enhanced in IL-4 deficient (IL-4$^{-/-}$) mice compared to wild-type controls. The effect of IL-4 modulation on post-immunization responses may be mediated by specific members of the STAT family and/or the master transcription factors bcl-6 and blimp-1 in antigen-specific B and T cells. These data elucidate a novel role for the anti-IL-4 mAb and IL-4:anti-IL-4 mAb complexes in programming GC-dependent T cell-dependent B cell differentiation for achieving optimal post-vaccination antibody responses and increase the subset of immunized subjects achieving clinical efficacy. Additionally, these data suggested that combining a vaccine with interleukins, interleukin:mAb complexes, anti-interleukin mAb, or anti-interleukin receptor mAb is a novel application.

Moreover, use of anti-interleukin mAb and/or anti-interleukin receptor mAb can improve vaccines that require high levels of antibody levels against pathogens, cancer, or agents of biological or chemical warfare (e.g., small molecule toxins).

Individual responses to vaccines for substance use disorder depended, at least in part, on the frequency of naïve and early-activated vaccine-specific B and T cells before and shortly after immunization. Effective individual responses correlated the magnitude of GC activation over GC-independent pathways. These data suggest that vaccines for substance use disorder can improve efficacy by incorporating immunization strategies that skew the T cell-dependent B cell differentiation toward GC formation.

Figure 8:
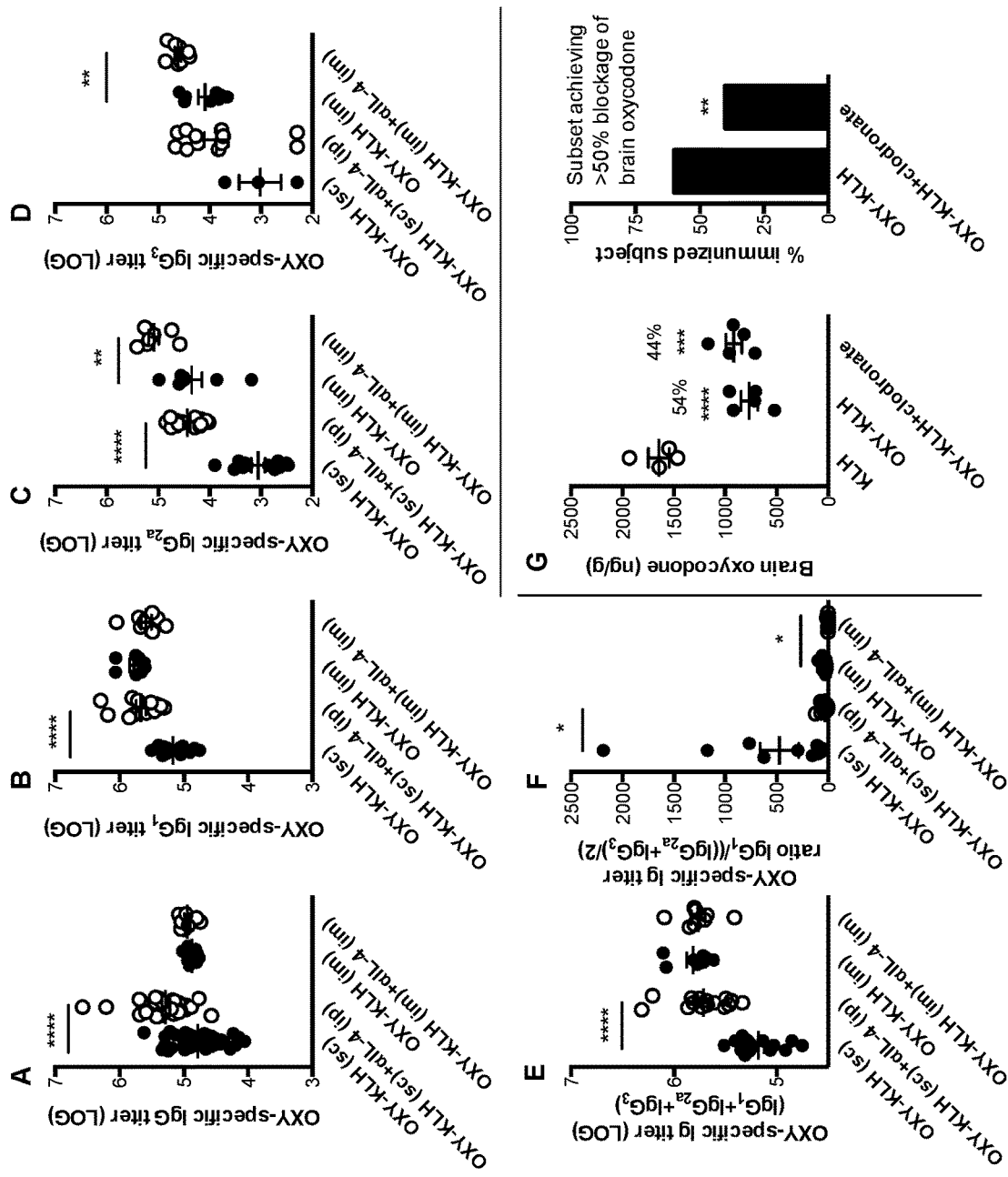
FIG. 8. Depletion of IL-4 increased the quantity and quality of the post-immunization anti-oxycodone serum antibody response and activated antibody-dependent phagocytosis activities. A first study analyzed antibody subclasses in mice immunized with OXY-KLH in alum with or without the anti-IL-4 mAb treatment. Data in panels (A-F) are from the same subjects as in FIGS. 5, 6, and 7A-C. IgG subclass analysis was performed on a representative sample randomly selected from each group (n=5-6 mice/group). Shown the analysis of oxycodone-specific serum IgG antibody: (A) total oxycodone-specific IgG titers; (B) $IgG_1$; (C) $IgG_{2a}$; (D) $IgG_3$; (E) $IgG_1+IgG_{2a}+IgG_3$; and (F) $IgG_1/((IgG_{2a}+IgG_3)/2)$, a measure of Th2 over Th1 activation. (G) In a follow-up independent experiment, mice were immunized with either KLH or OXY-KLH (n=5). On day 34, a group of mice immunized with OXY-KLH received liposome-encapsulated clonodrate to deplete macrophages, and 24 hours later challenged with 5.0 mg/kg oxycodone. Preventing macrophage activity reduced OXY-KLH efficacy in blocking oxycodone brain distribution and the subset (%) of immunized mice showing efficacy. In the figure, anti-IL-4 mAb is described as αIL-4. Statistical symbols: *$p<0.05$, $p<0.01$, *$p<0.001$, ****$p<0.0001$.
Figure 9:
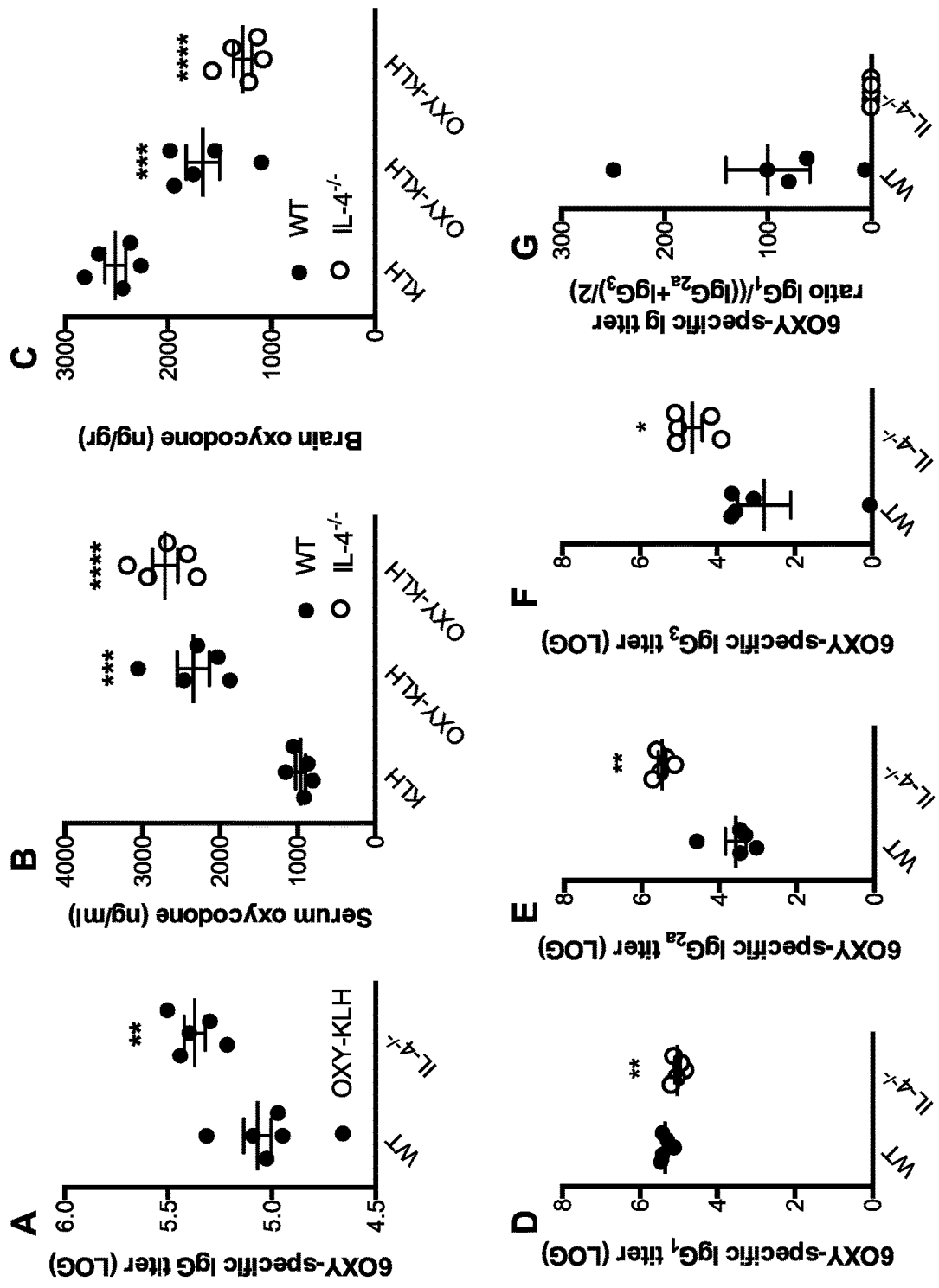
FIG. 9. Genetic ablation of IL-4 reproduces the effects of IL-4 depletion confirming that treatment with an anti-IL-4 mAb increases the efficacy of an oxycodone vaccine by IL-4 blockage. IL-4 deficient ($IL-4^{-/-}$) mice and wild-type (WT) controls were immunized with KLH or OXY-KLH in alum. After immunization: (A) oxycodone-specific IgG antibody titers, effect of immunization on oxycodone distribution to (B) serum and (C) to the brain. Antibody subclass analysis: (D) $IgG_1$; (E) $IgG_{2a}$; (F) $IgG_3$; (G) $IgG_1/((IgG_{2a}+IgG_3)/2)$. Statistical symbols: *$p<0.05$, $p<0.01$, *$p<0.001$, ****$p<0.0001$.
Figure 11:
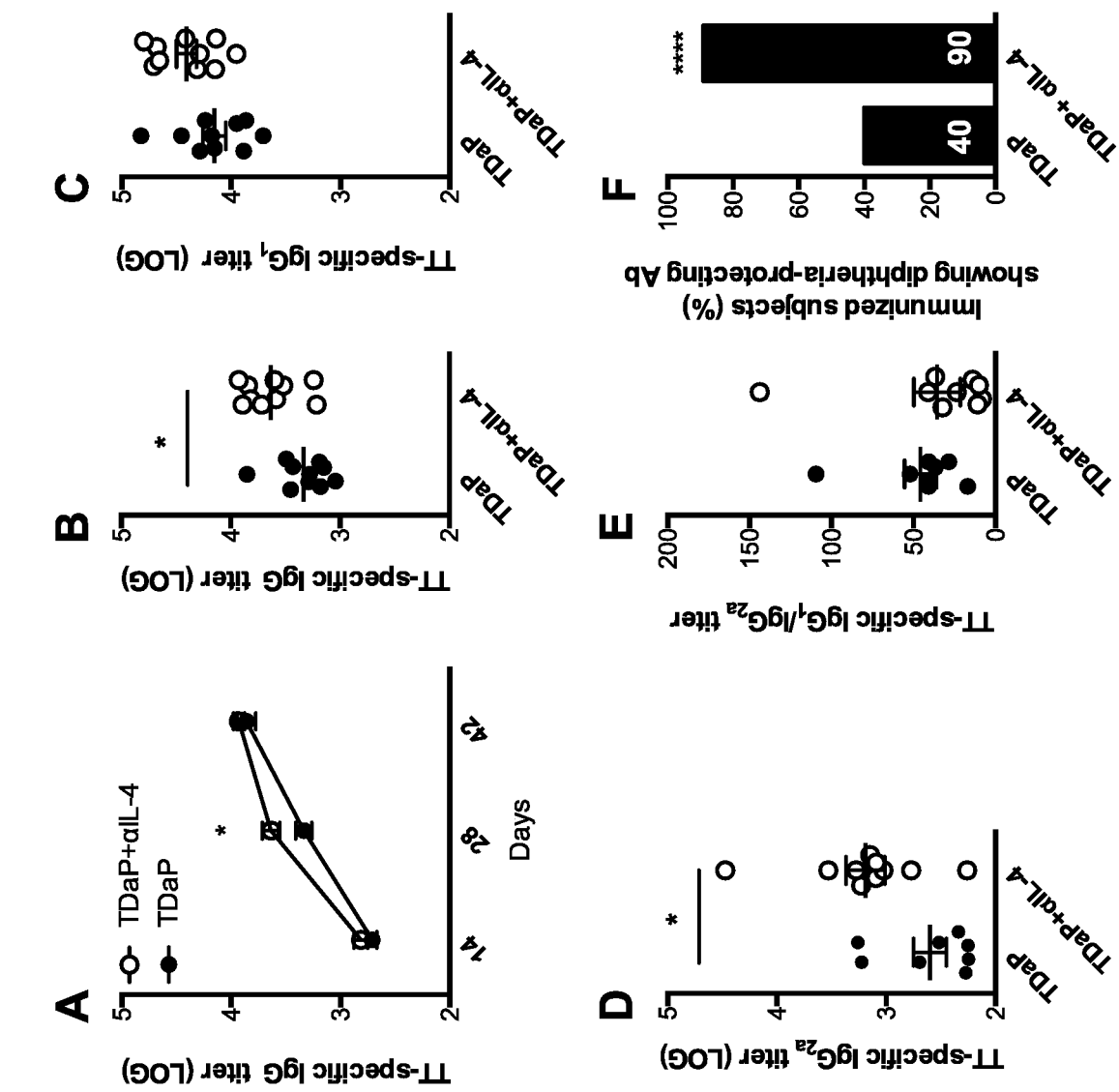
FIG. 11. Blockage of IL-4 signaling via anti-IL-4 mAb depletion enhances induction of antibody titers specific for tetanus toxoid and the fraction of immunized subjects showing protection against the diphtheria toxin. Mice were immunized with a commercially available tetanus toxoid, diphtheria, and acellular pertussis (TDaP) vaccine with or without the anti-IL-4 mAb. Serum TT-specific IgG, $IgG_1$ and $IgG_{2a}$ antibody titers were analyzed by ELISA. (A) TT-specific IgG titer over time. (B-F) A more detailed analysis of TT-specific IgG titers was performed on day 28 after the first immunization: (B) IgG; (C) $IgG_1$; (D) $IgG_{2a}$; (E) ratio of $IgG_1/IgG_{2a}$; (F) percentage of immunized subjects exhibiting anti-diphtheria antibodies. Data are mean±SEM. Anti-IL-4 mAb is described as αIL-4. Statistical symbols: *$p<0.05$.

This disclosure shows that interleukin signaling can be targeted to reprogram germinal center formation for enhancing efficacy of vaccines for substance use disorder. A model anti-drug vaccine (6OXY-KLH vaccine) was co-administered with IL-4, IL-6, IL-21, anti-IL-4 mAb, IL-4:anti-IL-4 mAb complexes, an anti-IL-2αR mAb (anti-CD25), or an anti-IL-7αR mAb (anti-CD127, not shown). FIGS. 8, 9, and 11 show data indicating that combining a vaccine with an anti-IL-4 mAb increases the production of antigen-specific $IgG_{2a}$ and $IgG_3$. This approach also can be used in research setting in immunization campaigns aiming at isolation of IgG$_{2a}$ vs. IgG$_1$ monoclonal antibodies. In some cases, an anti-IL-4 mAb could be administered in combination with the target vaccine to a mouse, rat, horse, llama, or other laboratory or farm animal used to produce and isolate either polyclonal antibodies (e.g., anti-venom polyclonal serum in horses), or monoclonal antibodies (e.g., single domain mAb in llamas).

Thus, this disclosure describes a method for treating drug use in a subject. The method generally includes co-administering to the subject a composition of at least two components (e.g., vaccine and a cytokine signaling immunomodulator, either with or without one or more modulators). The first component includes a vaccine that includes a derivative of the drug conjugated to a carrier polypeptide so that the conjugate is effective to induce production of antibody that specifically binds to the drug. In many cases, a small molecule drug, by itself, may be of insufficient size to induce antibody production in a subject. Conjugating the drug, or a derivative thereof, to a carrier polypeptide can induce antibody production directed against the drug moiety of the conjugate. The second component includes a cytokine signaling immunomodulator effective to increase production of the antibody.

As used herein, a "cytokine signaling immunomodulator" refers to a compound that directly induces or inhibits cytokine signaling in contrast to, for example, an adjuvant (e.g., alum, CpG, or imidoazoquinoline amines) that affect cytokine signaling only indirectly through another signaling pathway. A "cytokine signaling immunomodulator" can be a biological compound, such as, for example, interleukin, an antibody against an interleukin, an antibody against an interleukin receptor, an interleukin/monoclonal antibody complex, or a peptide ligand for an interleukin receptor. In other cases, a "cytokine signaling immunomodulator" can be a small molecule (e.g., STAT or mTOR ligand) that directly induces or inhibits cytokine signaling. For instance, the anti-IL-4 mAb inhibits exogenous or endogenous IL-4 from binding to the IL-4 receptor. In certain embodiments, a "cytokine signaling immunomodulator" can include a compound that targets the anti-IL-4 receptor (e.g., a peptide, antibody, antibody fragment, or small molecule ligand).

In another aspect, this disclosure describes a method for treating an infectious disease in a subject. Generally, the method involves co-administering a cytokine signaling immunomodulator and a vaccine that includes an immunogen effective for treating the infectious disease.

In another aspect, this disclosure describes a method for generating selected antibody responses in a research animal or farm animal. Generally, an anti-IL-4 mAb is administered in combination with a target vaccine to a mouse, rat, horse, llama, or other animal used to produce and isolate either polyclonal antibodies (e.g., anti-venom polyclonal serum in horses), or monoclonal antibodies (e.g., single domain mAb in llamas) of a specific subclass.

As used herein, the term "treat" or variations thereof refer to reducing, limiting progression, ameliorating, or resolving, to any extent, the symptoms or signs related to a condition. "Symptom" refers to any subjective evidence of disease or of a patient's condition. "Sign" or "clinical sign" refers to an objective physical finding relating to a particular condition capable of being found by one other than the patient.

Also as used herein, the term "co-administered" refers to two or more components of a combination administered so that the therapeutic effects of the combination can be greater than the therapeutic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. For example, in one exemplary embodiment, co-administering can refer to co-administering the two components in, for example, the same syringe (e.g., OXY-KLH+IL-4) or co-administering to the subject by different routes of administration (e.g., OXY-KLH given intramuscularly plus anti-IL-4 mAb given intraperitoneally or intravenously).

As used herein, the term "antibody" refers to immunoglobulin that specifically binds to an antigen. "Antibody," used without an article, is used collectively to refer to immunoglobulin encompassing a monoclonal antibody preparation (i.e., having a single molecular species of immunoglobulin) and/or a polyclonal antibody preparation (i.e., having more than one molecular species of immunoglobulin). As used herein, the term "specific" and variations thereof refer to having a differential or a non-general affinity, to any degree, for a particular target.

Figure 5:
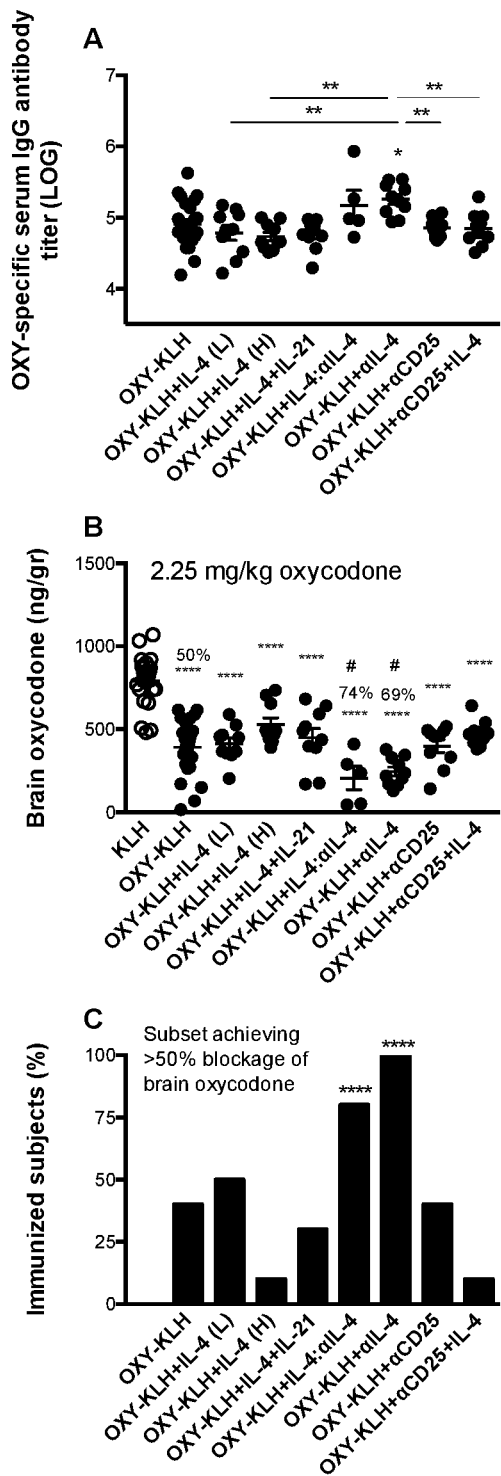
FIG. 5. In vivo screening of cytokine-based immunomodulators in combination with an oxycodone vaccine in mice. Modulation of IL-4 signaling by means of IL-4:anti-IL-4 immune complexes and/or an anti-IL-4 mAb enhanced anti-oxycodone antibody titers, vaccine efficacy in blocking distribution of oxycodone to the brain, and the subset of immunized subjects that showed vaccine efficacy. Male BALB/c mice were immunized subcutaneously on days 0, 14, and 28, and challenged with 2.25 mg/kg oxycodone subcutaneously a week after the third immunization. Mice received unconjugated KLH, OXY-KLH, or OXY-KLH in combination with IL-4 (30,000 IU, low dose (L), subcutaneously), IL-4 (60,000 IU, high dose (H), subcutaneously), IL-4 plus IL-21 (60,000 IU total, subcutaneously), IL-4:anti-IL-4 mAb (subcutaneously, 30,000 IU and 0.5 mg of mAb mixed prior to injection), anti-IL-4 mAb (1.0 mg per mouse, intraperitoneally), anti-IL-2 alpha receptor mAb (anti-CD25, 1.0 mg per mouse, intraperitoneally), or anti-CD25 mAb (1.0 mg per mouse, intraperitoneally) plus IL-4 (30,000 IU, subcutaneously). The OXY-KLH and the unconjugated KLH were absorbed on alum adjuvant prior to administration. Interleukins were administered at 0 days, 14 days, and 28 in combination with each immunization. The mAb were administered two days prior and one day after the first immunization (0.5 mg each injection, total 1.0 mg per mouse). In immunized mice: (A) oxycodone-specific IgG antibody titers, (B) effect of immunization on oxycodone distribution to the brain, and (C) fraction (%) of immunized subjects that showed more than 50% reduction in oxycodone distribution to the brain compared to the mean brain concentration in the KLH control group. Data are mean±SEM. Data shown are from at least two independent experiments (n=5-10). Percentages (%) above bars indicate reduction compared to the KLH group. In the figure, anti-IL-4 mAb and anti-CD25 mAb are described as αIL-4 and αCD25. Statistical symbols: *p<0.05, p<0.001, **p<0.0001 compared to KLH control, and brackets or # indicate significance between groups.
Figure 6:
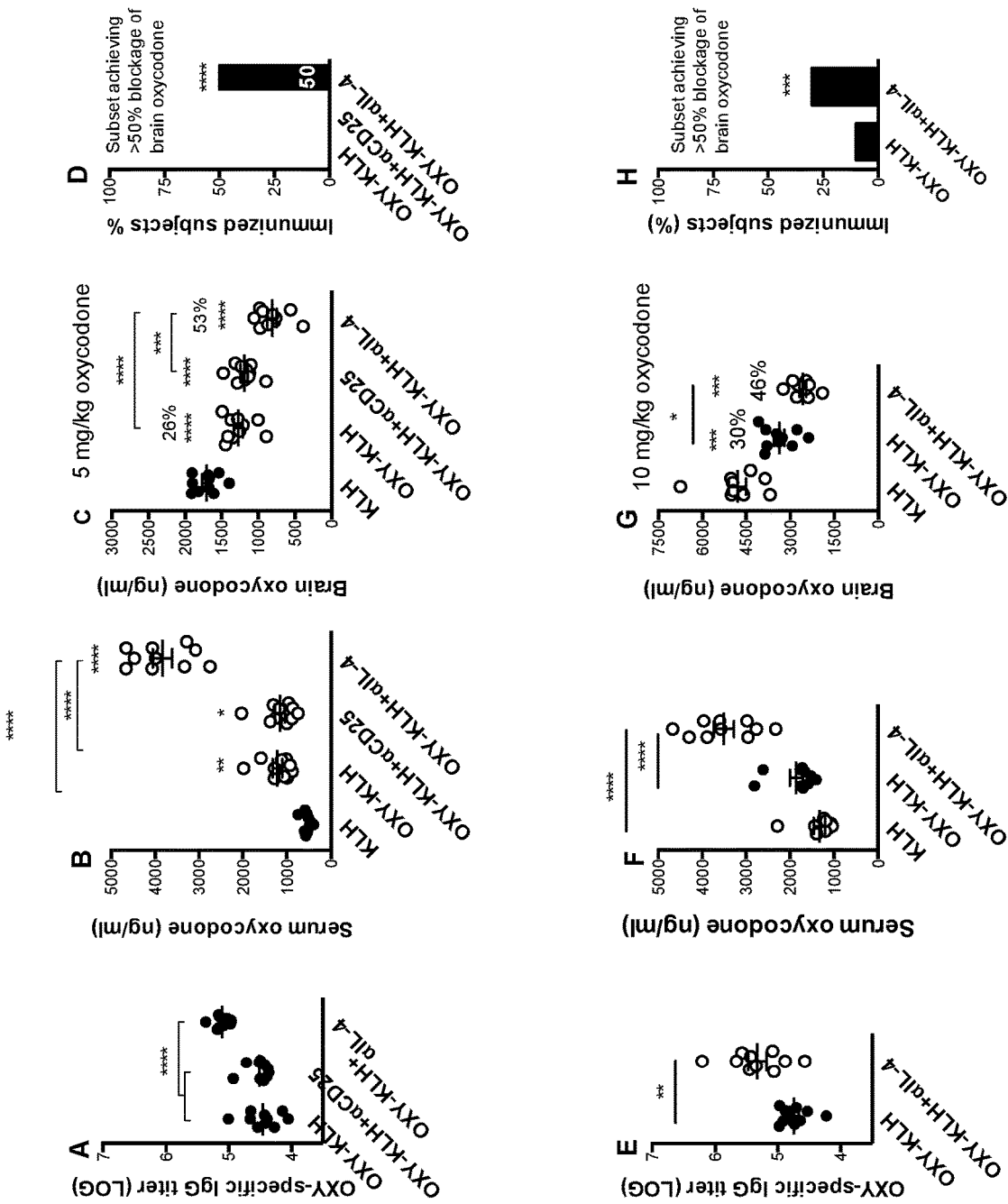
FIG. 6. In vivo blockage of IL-4 increased vaccine efficacy against high doses of oxycodone (5 mg/kg or 10 mg/kg challenges). Male BALB/c mice were immunized with OXY-KLH or unconjugated KLH as control subcutaneously on days 0, 14 and 28, and challenged with oxycodone one week after the third immunization. In a first experiment, mice received KLH, OXY-KLH, or OXY-KLH in combination with anti-CD25 mAb (1.0 mg, intraperitoneally), or anti-IL-4 mAb (1.0 mg, intraperitoneally) and challenged with 5.0 mg/kg oxycodone. In a follow-up experiment, mice received KLH, OXY-KLH, or OXY-KLH in combination with anti-IL-4 mAb (1.0 mg, intraperitoneally) and challenged with 10.0 mg/kg oxycodone. After immunization: (A) oxycodone-specific IgG antibody titers, effect of immunization on oxycodone distribution to serum (B) and to the brain (C), and (D) fraction (%) of immunized subjects that showed more than 50% reduction in oxycodone distribution to the brain compared to the mean brain concentration in the KLH control group. Panels (E-H) convey the same information as the upper panel (titers, distribution to serum and brain, and % of responders), but cohort of mice received a 10 mg/kg oxycodone challenge. Data are mean±SEM. Data shown are from at least two independent experiments (n=10). Percentages (%) above bars indicate reduction compared to the KLH group. In the figure, anti-IL-4 mAb and anti-CD25 mAb are described as αIL-4 and αCD25. Statistical symbols: *p<0.05, p<0.001, **p<0.0001 compared to KLH control, and brackets to indicate significance between groups.
Figure 7:
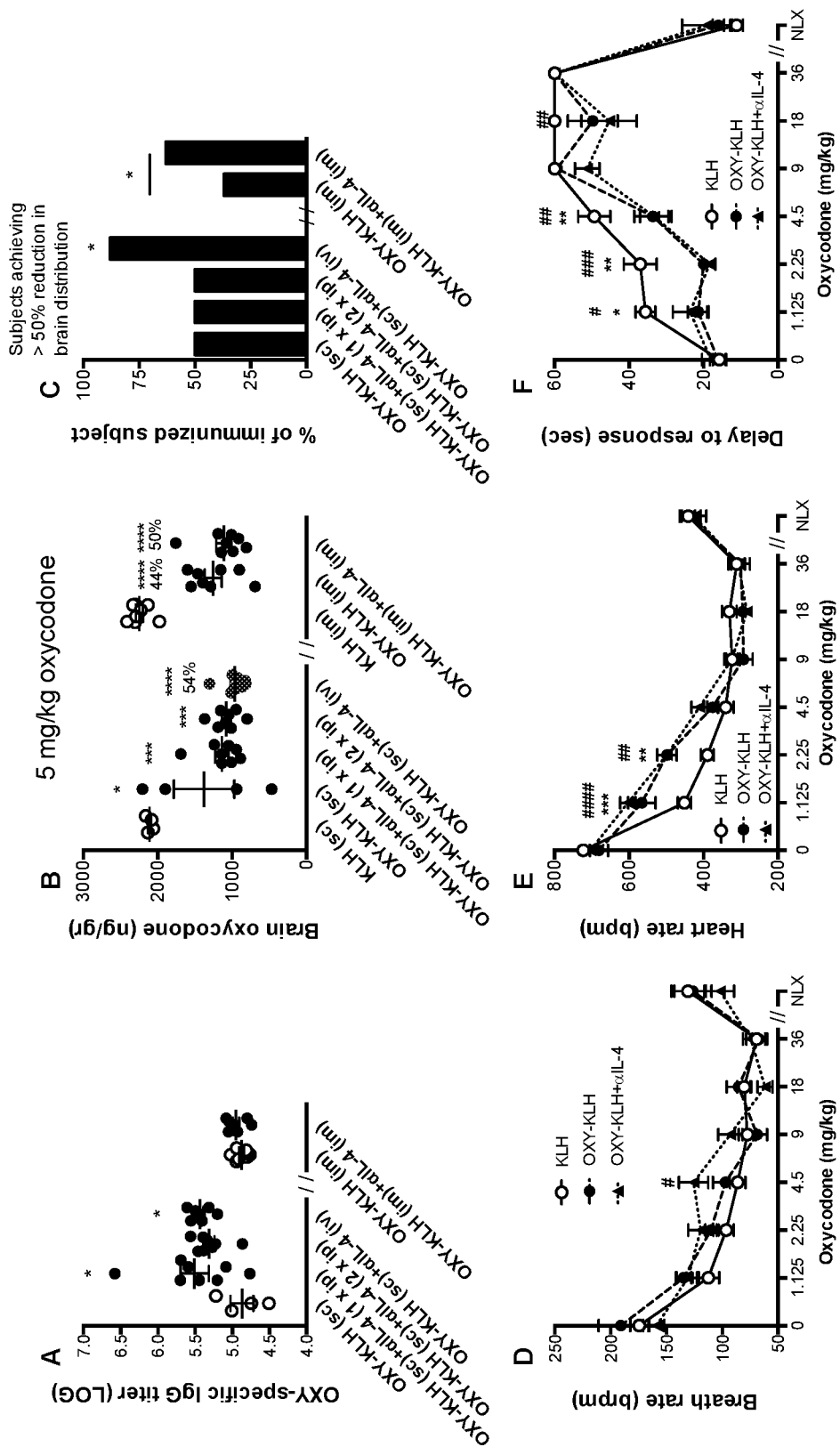
FIG. 7. The immunogenicity and efficacy of the oxycodone vaccine combined with the anti-IL-4 mAb is conserved across clinically-relevant immunization regimens, attenuated oxycodone-induced toxicity and behavioral effects, and did not interfere with naloxone reversal of opioid-induced toxicity. Two independent cohorts of BALB/c mice were immunized with OXY-KLH or unconjugated KLH on days 0, 14 and 28, and tested for vaccine efficacy a week after the third immunization. Mice received OXY-KLH subcutaneously or intramuscularly. Anti-IL-4 mAb was administered intraperitoneally, intravenously, or intramuscularly. In a first cohort, mice were challenged with 5.0 mg/kg oxycodone: (A) oxycodone-specific IgG titers; (B) oxycodone brain concentrations; and (C) percentage of subjects that showed more than 50% reduction in oxycodone distribution to the brain compared to the KLH group. Data are mean±SEM. Data shown are from one experiment (n=5-8). Percentages (%) above bars indicate reduction compared to the KLH group. In the figure, anti-IL-4 mAb is described as αIL-4. Statistical symbols: *$p<0.05$, $p<0.001$, **$p<0.0001$ compared to KLH control, and brackets to indicate significance between groups. In a second cohort, immunized mice were tested for opioid-induced respiratory depression, heart rate and antinociception. Oxycodone was administered subcutaneously every 15 minutes at increasing doses and the doses listed are the cumulative dose received. Naloxone 0.1 mg/kg subcutaneously was administered 15 minutes after the final oxycodone dose to reverse opioid effects. (D) Breath rate, (E) heart rate, and (F) antinociception on a hot plate. *$p<0.05$, $p<0.01$, *$p<0.001$ for the difference between OXY-KLH and KLH. # $p<0.05$, ## $p<0.01$, ### $p<0.001$, and #### $p<0.0001$ for the difference between OXY-KLH plus anti-IL-4mAb and KLH. Data are mean±SEM. Data shown are from one experiment (n=8).

In some embodiments, the immunomodulator can include a complex formed between IL-4 and an antibody that specifically binds to IL-4. While the complex can form naturally through an affinity interaction between the antibody and IL-4, the immunomodulator can involve IL-4 and the antibody being complexed through an affinity interaction or through one or more covalent bonds. FIG. 5-7 show data indicating that administering such a composition (e.g., vaccine plus immunomodulator) to a subject increases serum IgG antibodies that specifically bind the free drug in serum and decreases the amount of drug that crosses the blood-brain barrier. In some embodiments, the immunomodulator can include anti-IL-4 mAb. FIG. 5-7 show data indicating that administering such composition to a subject increases the serum IgG response that decreases the amount of drug reaching the brain. FIG. 7 shows data indicating that administering such a composition to a subject reduced opioid-induced toxicity including respiratory depression and bradycardia. FIG. 7 also shows data indicating that administering such composition to a subject does not interfere with pharmacological reversal of opioid-induced toxicity by the opioid antagonist naltrexone. Thus, the vaccine blocks opioid-induced toxicity that may contribute to overdose. Moreover, the combination of vaccine plus anti-IL-4 mAb enhanced vaccine efficacy against toxicity from oxycodone. FIG. 8 shows data indicating that administering such a composition to a subject increases the quantity and quality of the serum IgG response by activating various IgG subclasses, and that such a composition may activate antibody-dependent effector functions, such as phagocytosis, which removes additional free drug and thus increases vaccine efficacy. FIG. 9 shows data indicating that genetic depletion of IL-4 increases vaccine efficacy against oxycodone providing additional mechanistic evidence for this approach.

In some embodiments, the immunomodulator can include an antibody that specifically binds to IL-2 receptor a chain (IL-2αR, also known as CD25). While described herein in the context of exemplary embodiments in which the immunomodulator includes IL-4, IL-6, IL-21, mAb anti-IL-4, and mAb anti-IL-2αR, the immunomodulator component can include other immunomodulators such as, for example, interleukin, a small molecule that modulates interleukin signaling (e.g., JAK/STAT ligand), a mAb that specifically binds an interleukin, and/or a mAb that specifically binds an interleukin receptor (e.g., mAb anti-IL-7αR).

Figure 10:
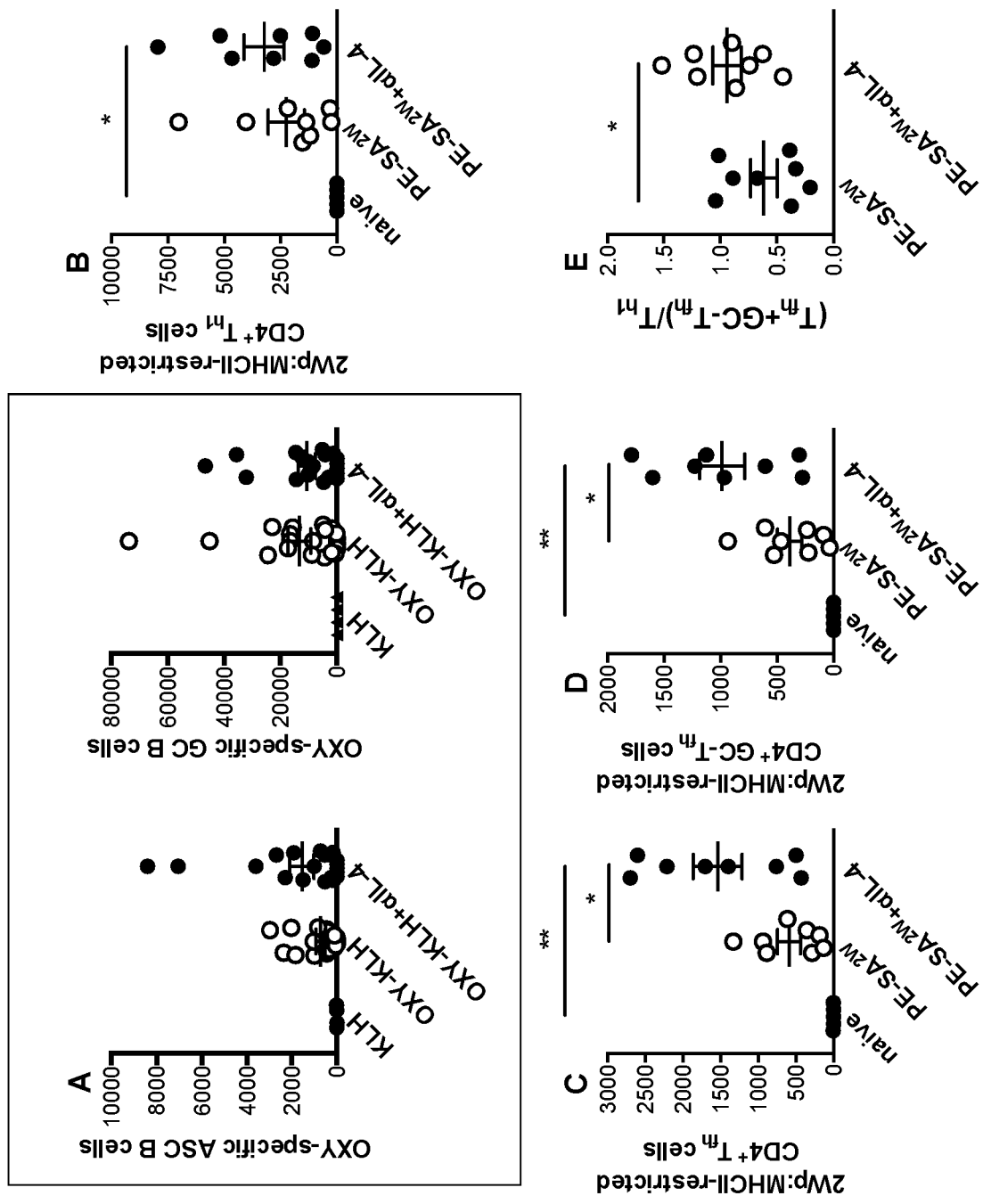
FIG. 10. IL-4 depletion does not impair antigen-specific plasma and germinal center B cell expansion, but significantly increases differentiation of antigen-specific T cells after immunization. BALB/c mice were immunized once with KLH, OXY-KLH in alum adjuvant, and OXY-KLH in alum adjuvant plus the anti-IL-4 mAb (KLH, n=4, OXY-KLH, n=20, and OXY-KLH plus anti-IL-4 mAb, n=20). Analysis of B cell lymphocyte populations was performed seven days after immunization. Briefly, OXY-specific B cells were first isolated by magnetic enrichment using biotinylated oxycodone-based haptens conjugated to SA-PE and then analyzed by multi-parameter flow cytometry. Analysis of germinal center B cells shortly after immunization is a marker of germinal center formation in secondary lymphoid organs. (A) the number of OXY-specific antibody secreting B cells (ASC) and germinal center (GC) B cells was not affected by IL-4 depletion. (B-E) In a separate study, C57BL/6 mice were immunized with a model immunogen consisting of PE-SA conjugated to the biotinylated 2W peptide ($PE-SA^{2W}$). Groups were as follows: naive, $PE-SA^{2W}$ and $PE-SA^{2W}$ plus the anti-IL-4 mAb. At seven days after immunization, lymph nodes and spleens were collected for analysis of antigen-specific T cell populations. Using a two-step procedure, 2W-specific T cells were first isolated by magnetic enrichment using 2W conjugated to soluble MHCII receptors tetramerized on SA-PE and then analyzed by flow cytometry using standard surface and intracellular markers. (B) $CD4^+$ Th1 cells; (C) $CD4^+$ $T_{FH}$ cells; (D) $CD4^+$ GC-$T_{FH}$ cells; (E) ($T_{FH}$+GC-$T_{FH}$)/Th1. Data are mean±SEM. Statistical symbols: **$p<0.01$.
Figure 12:
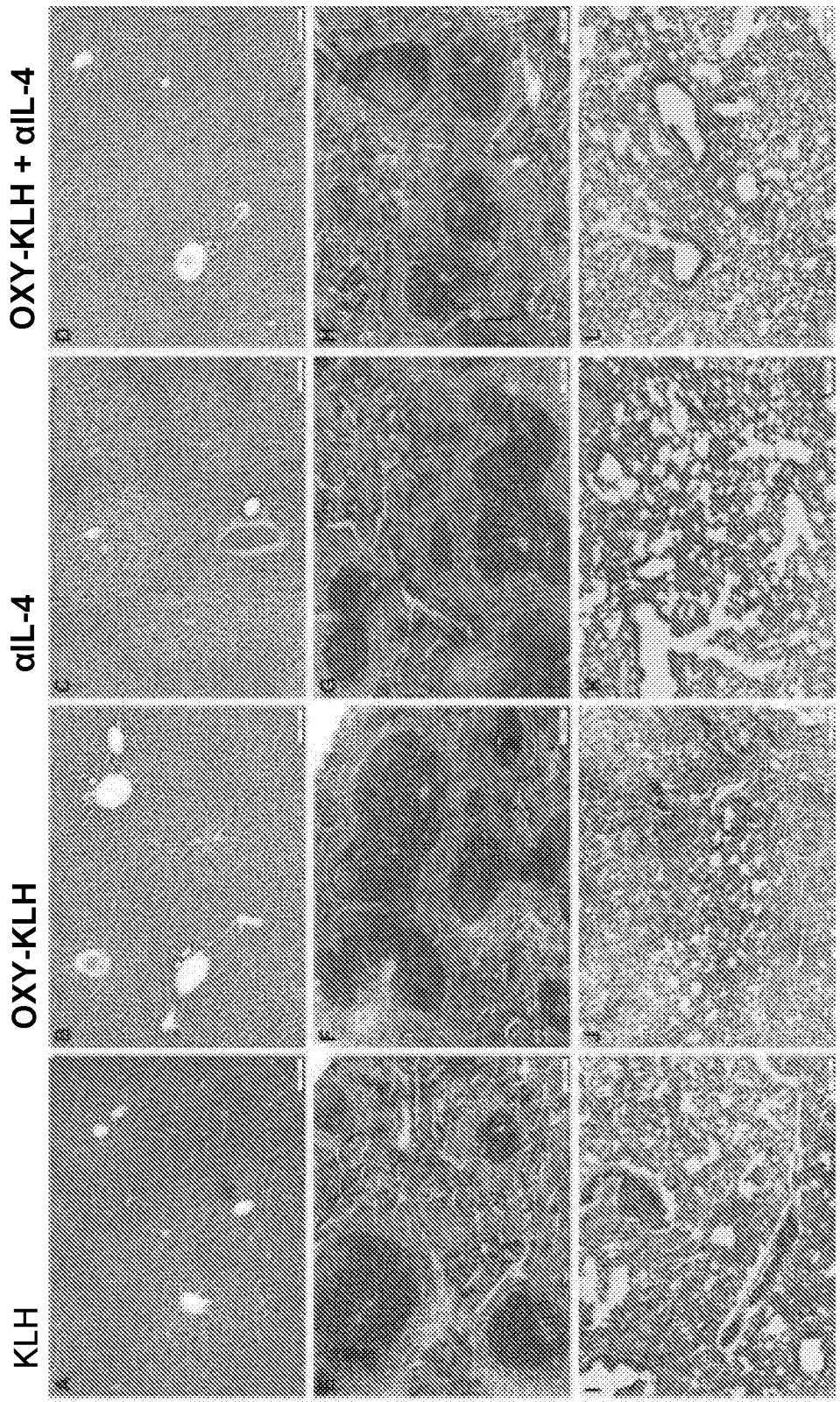
FIG. 12. Co-administration of vaccines and an anti-IL-4 mAb is safe. Histopathology across four treatment groups. (A-D) Images show occasionally moderate vacuolar change within the centrolobular hepatocytes that was similar in severity across four treatment groups (KLH, OXY-KLH, anti-IL-4 mAb, and OXY-KLH plus anti-IL-4 mAb). (E-H) No significant pathology was observed in the spleen. (I-L) In all treatment groups, the lungs demonstrated regions containing mild to occasionally moderately increased numbers of inflammatory cells, principally lymphocytes with fewer neutrophils, in the interstitium with concurrent congestion. Occasionally, these regions of were centered on lymphocyte-rich lymphatic vessels. The severity of the lung pathology was similar across the four treatment groups. No significant pathology was identified in the kidney, heart, thymus, stomach, small intestine, large intestine, and pancreas. In the figure, anti-IL-4 mAb is described as αIL-4.

While described herein in the context of exemplary embodiments in which the immunotherapy is directed against a small molecule drug for treating drug use, the immunomodulatory component may be co-administered with existing vaccines directed against, for example, one or more antigens associated with an infectious disease or other small molecules or peptides associated with non-communicable diseases (e.g., cancer, Alzheimer's disease, or cardiovascular disease). FIG. 10A shows data indicating that treatment with an anti-IL-4 mAb does not impair GC formation in response to small molecule haptens, suggesting that hapten-specific B cell responses may be partially IL-4 independent. In contrast, FIG. 10B-E show that treatment with anti-IL-4 mAb, administered with a peptide-protein conjugate immunogen, increases peptide-specific CD4$^+$ T cell differentiation into peptide-specific GC-T$_{fh}$ cells, a T cell subset responsible for B cell help. FIG. 11 shows data indicating that an anti-IL-4 monoclonal antibody, administered with a tetanus diphtheria acellular pertussis (TDaP) vaccine increases serum IgG titer compared to administering the vaccine alone, and that inhibiting IL-4 increases IgG$_{2a}$ subclass responses, which increased antibody production against diphtheria. The same approach could be used to increase the post-immunization antibody response against a small antigen (e.g., a carbohydrate, a small molecule, or a peptide) or purified subunits associated with other infectious diseases or non-communicable chronic diseases. Pre-clinical toxicology data (Table 1) and histopathology data (FIG. 12) supporting the safety for this approach.

chimeric mAb, or a humanized mAb). In this context, the mAb can include the full monoclonal antibody or a fragment thereof such as, for example, a single domain antibody fragment.

The compositions described herein may be formulated with a pharmaceutically acceptable carrier. As used herein, a "pharmaceutically acceptable carrier" includes any solvent, dispersion medium, vehicle, coating, diluent, antibacterial, and/or antifungal agent, isotonic agent, absorption delaying agent, buffer, carrier solution, suspension, colloid, polymers, nanoparticles, liposomes, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with an active agent without causing any undesirable biological effects or interacting in a deleterious manner with any of the other components of the pharmaceutical composition in which it is contained.

The vaccine and the immunomodulator may therefore be formulated into a pharmaceutical composition or, as described above, multiple pharmaceutical compositions. A pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray, aerosol, or gel). A composition also

TABLE 1

| Treatment | Total protein (g/dl) | Total bilirubin (mg/dl) | ALT (U/L) | AST (U/L) | Urea nitrogen (mg/dl) | Cholesterol (mg/dl) | Body weight (g) |
| --- | --- | --- | --- | --- | --- | --- | --- |
| KLH | 5.7 ± 0.32 | 0.2 ± 0.10 | 71.6 ± 3.2 | 626 ± 24.7 | 20 ± 1.5 | 161 ± 10.4 | 26.5 ± 0.39 |
| OXY-KLH | 5.4 ± 0.17 | 0.3 ± 0.11 | 74 ± 4.7 | 709 ± 51.6 | 20 ± 1.0 | 154 ± 11.0 | 27.4 ± 0.75 |
| Anti-IL-4 mAb | 5.8 ± 0.06 | 0.46 ± 0.03 | 104 ± 9.5 | 605 ± 253 | 27 ± 2.8 | 163 ± 0.3 | 27.7 ± 0.72 |
| OXY-KLH + Anti-IL-4 mAb | 5.5 ± 0.26 | 0.27 ± 0.09 | 101 ± 32.3 | 840 ± 286 | 24 ± 1.0 | 158 ± 13.0 | 27.1 ± 0.24 |

Data are expressed as mean ± SEM.

Serum biochemistry parameters in BALB/C mice treated with KLH, OXY-KLH, anti-IL-4 mAb, or anti-IL-4 mAb plus OXY-KLH. Protein, bilirubin, ALT (alanine aminotransferase), urea nitrogen, and total cholesterol were in the normal range. The values for AST (aspartate aminotransferase) were higher among groups, perhaps as a result of muscle injury due from the injections.

While described herein in the context of an exemplary embodiment using recombinant mouse interleukins with rat anti-mouse anti-interleukin mAb to enhance vaccine efficacy in mice, the methods described herein can be practiced using any suitable combination of interleukin from any source and any anti-interleukin antibody from any source. Thus, exemplary alternative embodiments include the use of, for example, recombinant human interleukins and an anti-human anti-interleukin mAb of any suitable origin (e.g, a mouse anti-human mAb, a llama anti-human mAb, a can be administered via a sustained or delayed release. In embodiments in which the vaccine and the immunomodulator are formulated into separate formulations, each component may be administered by a route independent of the other component.

Thus, vaccine and/or immunomodulator may be provided in any suitable form including but not limited to a solution, a suspension, an emulsion, a spray, an aerosol, or any form of mixture. The composition may be delivered in formulation with any pharmaceutically acceptable excipient, carrier, or vehicle. A formulation may be conveniently presented in unit dosage form and may be prepared by methods well known in the art of pharmacy. Methods of preparing a composition with a pharmaceutically acceptable carrier include the step of bringing the active agent—i.e., the vaccine and/or immunomodulator—into association with a pharmaceutically acceptable carrier that constitutes one or more accessory ingredients. In some embodiments, for example, a formulation may be prepared by uniformly and/or intimately bringing the active compound into association with a liquid pharmaceutically acceptable carrier, a finely divided solid pharmaceutically acceptable carrier, or both, and then, if necessary, shaping the product into the desired formulations.

The amount of vaccine and immunomodulator that is administered can vary depending on various factors including, but not limited to, the specific vaccine being administered, the specific immunomodulator being administered, the weight, physical condition, and/or age of the subject, and/or the route of administration. Thus, the absolute weight of active agents included in a given unit dosage form can vary widely, and depends upon factors such as the species, age, weight and physical condition of the subject, and/or the method of administration. Accordingly, it is not practical to set forth generally the amount that constitutes an amount of active agents effective for all possible applications. Those of ordinary skill in the art, however, can readily determine the appropriate amount with due consideration of such factors.

For example, certain vaccines and/or certain immunomodulators may be administered at the same dose and frequency for which the vaccine and/or immunomodulator has received regulatory approval. In other cases, certain active agents may be administered at the same dose and frequency at which the drug is being evaluated in clinical or preclinical studies. One can alter the dosages and/or frequency as needed to achieve a desired level of antibody production. Thus, one can use standard/known dosing regimens and/or customize dosing as needed.

In some embodiments, the method can include administering sufficient immunomodulator to provide a dose of, for example, from about 100 ng/kg to about 50 mg/kg to the subject, although in some embodiments the methods may be performed by administering the immunomodulator in a dose outside this range. In some of these embodiments, the method includes administering sufficient immunomodulator to provide a dose of from about 10 µg/kg to about 5 mg/kg to the subject, for example, a dose of from about 100 µg/kg to about 1 mg/kg. In preliminary studies using a mouse model, the use of mAb doses within or below the human range (0.1-10 mg/kg) supported the efficacy and cost-effectiveness of this approach.

In some embodiments, the vaccine/immunomodulator composition may be administered, for example, from a single dose to multiple doses per week, although in some embodiments the method can be performed by administering the vaccine/immunomodulator composition at a frequency outside this range. In certain embodiments, the vaccine/immunomodulator composition may be administered at least once per month. In clinical trials of nicotine and cocaine vaccines, immunogens were administered once a month for 5-6 months followed by boosts at 3-6 months.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Figure 4:
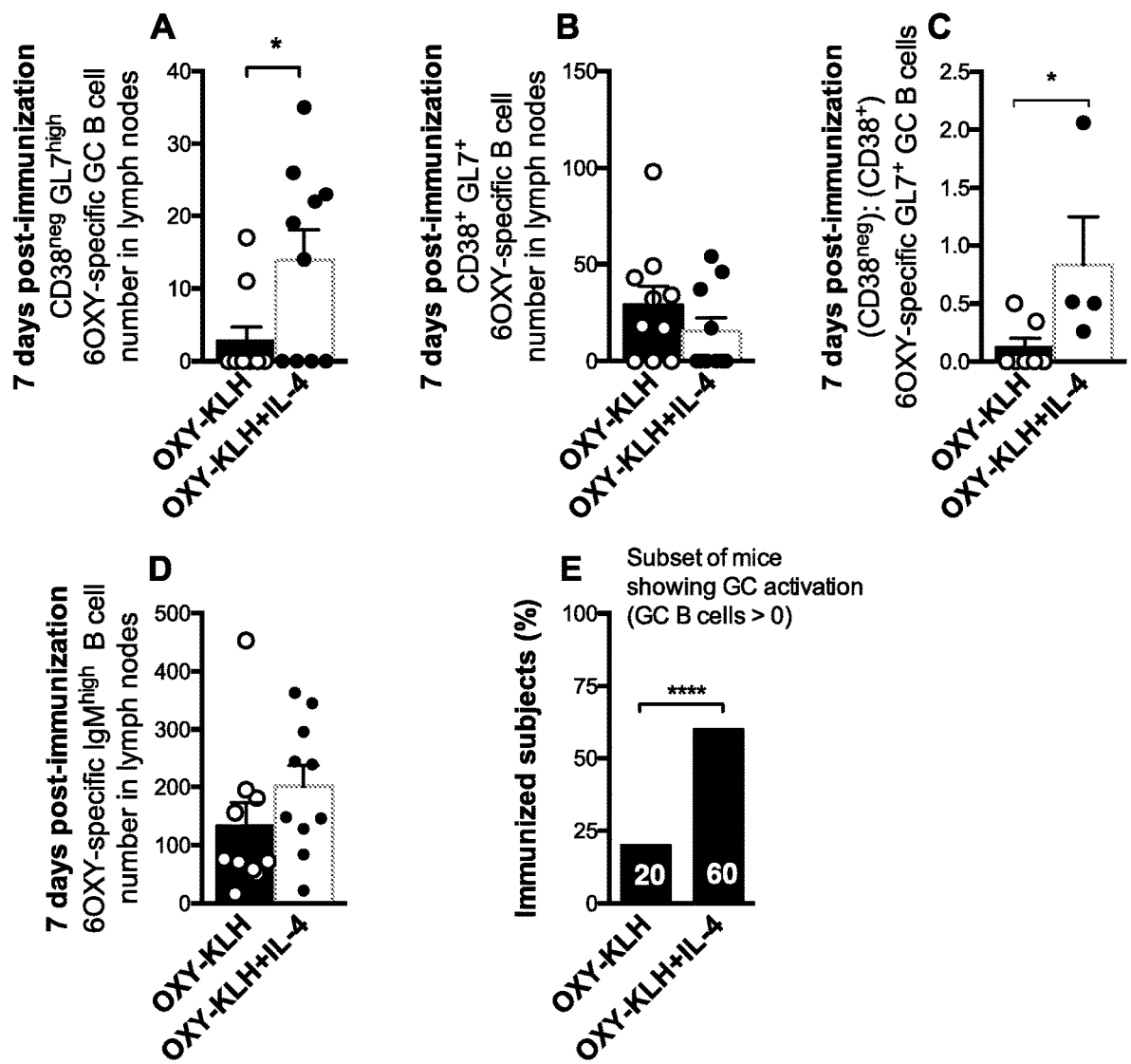
FIG. 4. IL-4 increased vaccine-specific GC B cells and post-vaccination GC formation. Mice were immunized subcutaneously once with the OXY-KLH vaccine adsorbed in alum adjuvant with saline or IL-4 (60,000 IU, subcutaneously). At seven days after immunization, lymph nodes and spleens were collected for analysis of antigen-specific B cell populations. Using a two-step procedure, OXY-specific B cells were first isolated by magnetic enrichment using biotinylated oxycodone-based haptens conjugated to streptavidin (SA) conjugated to the fluorescent protein phycoerythrin (PE) or a decoy reagent, and then analyzed by multi-parameter flow cytometry. (A) 6OXY-specific $CD38^{neg}$ $GL7^{high}$ "committed" GC B cells; (B) 6OXY-specific $CD38^+$ $GL7^+$ "uncommitted" GC B cells; (C) Ratio of 6OXY-specific ($CD38^{neg}$) to ($CD38^+$) $GL7^+$ B cells, a measure of GC activation and B cell commitment to GC-dependent pathways; (D) 6OXY-specific $IgM^{high}$ naive and memory B cells. Data shown are from two independent experiments and expressed as mean±SEM (n=10). (E) Chi-square analysis of the fraction (%) of immunized subjects that showed GC formation. Statistical symbols: *p<0.05, and ****p<0.001.

IL-4 increased vaccine-specific germinal center (GC) B cells and the fraction of subjects that showed post-vaccination GC formation. Mice were immunized subcutaneously once with OXY-KLH in alum adjuvant in combination with IL-4 (60,000 IU, Bio-Techne Corp., Minneapolis, MN). At seven days after immunization, lymph nodes and spleens were collected and analysis of 6OXY-specific B cells performed by magnetic enrichment paired with flow cytometry as previously described (Laudenbach et al., 2015. *J Immunol* 194(12):5926-5936). Results are shown in FIG. 4.

Example 2

Male BALB/c mice were immunized subcutaneously on days 0, 14, and 28, and challenged with 2.25 mg/kg oxycodone subcutaneously a week after the third immunization. Mice received unconjugated KLH, OXY-KLH, or OXY-KLH in combination with IL-4 (30,000 IU and 60,000 IU, subcutaneously), IL-4 plus IL-21 (60,000 IU total, subcutaneously), IL-4:anti-IL-4 mAb (subcutaneously, 30,000 IU and 0.5 mg of mAb mixed prior to injection), anti-IL-4 mAb (1.0 mg per mouse, intraperitoneally), anti-IL-2α receptor mAb (anti-CD25, 1.0 mg per mouse, intraperitoneally), or anti-CD25 mAb (1.0 mg per mouse, intraperitoneally) plus IL-4 (30,000 IU, subcutaneously). The OXY-KLH and the unconjugated KLH were absorbed on alum adjuvant prior to administration. Interleukins were administered at 0, 14 and 28 in combination with each immunization. Monoclonal antibodies were administered two days prior and one day after the first immunization. Recombinant mouse IL-4 and IL-21 were obtained from Bio-Techne Corp., Minneapolis, MN. The mAb anti-IL-4 (rat anti-mouse $IgG_1$, clone 11B11) and mAb anti-IL-CD25 (rat anti-mouse $IgG_1$, clone 7D4) were obtained from Bio X Cell, West Lebanon, NH Results are shown in FIG. 5.

Example 3

Male BALB/c mice were immunized with OXY-KLH or unconjugated KLH as control subcutaneously on days 0, 14 and 28, and challenged with oxycodone a week after the third immunization. In a first experiment, mice received KLH, OXY-KLH, OXY-KLH in combination with anti-CD25 mAb (1.0 mg, intraperitoneally), or anti-IL-4 mAb (1.0 mg, intraperitoneally) and challenged with 5.0 mg/kg oxycodone. In a subsequent experiment, mice received KLH, OXY-KLH, and OXY-KLH in combination with anti-IL-4 mAb (1.0 mg, intraperitoneally) and challenged with 10.0 mg/kg oxycodone. Reagents were obtained as EXAMPLE 2. Results are shown in FIG. 6.

Example 4

Male BALB/c mice were immunized with OXY-KLH or unconjugated KLH as control on days 0, 14 and 28, and challenged with 5.0 mg/kg oxycodone a week after the third immunization. Mice received OXY-KLH subcutaneously or intramuscularly. The anti-IL-4 mAb was administered either intraperitoneally, intravenously, or intramuscularly. Results are shown in FIG. 7A-C.

Example 5

Male BALB/c mice immunized with either KLH, OXY-KLH, or OXY-KLH plus the anti-IL-4 mAb, as in EXAMPLE 4, were tested for opioid-induced respiratory depression, heart rate, and antinociception. Oxycodone was administered subcutaneously every 15 minutes at increasing doses and the doses listed are the cumulative dose received. Naloxone 0.1 mg/kg was administered subcutaneously 15 minutes after the final oxycodone dose to reverse opioid effects. Results are shown in FIG. 7D-F.

Example 6

Male BALB/c mice from EXAMPLES 2-4 were randomly selected for IgG subclass analysis (n=5-6 mice/group). ELISA plates were coated with 5 ng/well of OVA conjugate or unconjugated protein control in carbonate buffer at pH 9.6 and blocked with 1% gelatin. Primary antibodies were incubated with goat-anti-mouse IgG1, IgG2a, or IgG3 conjugated to horseradish peroxidase (Alpha Diagnostic International, Inc., San Antonio, TX) to measure oxycodone-specific serum IgG antibody subclass titers. Results are shown in FIG. 8.

Example 7

IL-4 deficient (IL-4$^{-/-}$) mice and wild-type (WT) controls (The Jackson Laboratory, Bar Harbor, ME, stock no. 002496 and 000651, respectively) were immunized subcutaneously with unconjugated KLH or OXY-KLH in alum on days 0, 14 and 28, and challenged with 5.0 mg/kg oxycodone a week after the third immunization. Analysis of OXY-specific IgG antibody titers was performed as EXAMPLE 5. Results are shown in FIG. 9.

Example 8

BALB/c mice were immunized once with OXY-KLH in alum adjuvant subcutaneously with or without the anti-IL-4 mAb (KLH, n=4, OXY-KLH, n=20, and OXY-KLH plus anti-IL-4 mAb, n=20) as described in EXAMPLE 2. Antibodies were given intraperitoneally in two separate 0.5 mg doses, three days prior to immunization and again one day after immunization. Analysis of OXY-specific B cells was performed by magnetic enrichment paired with flow cytometry as previously described (Laudenbach et al., 2015. J Immunol 194(12):5926-5936). Results are shown in FIG. 10A.

Example 9

C57Bl/6 mice were immunized with the model immunogen pycoerythryin (PE) conjugated to streptavidin (SA) and the PE-SA immunogen conjugated with a model T cell peptide (2W). C57BL/6 mice were immunized subcutaneously with 25 µg of a model immunogen consisting of PE-SA (ProZyme, Inc., Hayward, CA, PJRS25) conjugated the 2W peptide (PE-SA$^{2W}$), and adsorbed on alum adjuvant prior to injection. The biotinylated peptide was conjugated to streptavidin at a mole ratio of 4.5:1 in 0.01 M PBS for 30 minutes at a final concentration of 1 mg/ml, and purified by filtration (AMICON, 100 Kda cutoff EMD Millipore Corp., Billerica, MA) and centrifugation at 4000×g for 15 minutes at 4° C. Analysis of 2W-specific T cells was performed by tetramer-based magnetic enrichment and flow cytometry as described (Laudenbach et al., 2015. J Immunol 194(12):5926-5936). Antigen-specific $T_{FH}$ and GC-$T_{FH}$ were further characterized as described (Tubo et al., 2013. Cell 153(4):785-96). The biotinylated 2W peptide and the 2Wp:MHCII tetramers were a generous gift from Dr. Marc Jenkins at the University of Minnesota Center for Immunology. Results are shown in FIG. 10A.

Example 10

Male BALB/c mice were immunized subcutaneously on days 0, 14 and 28 with a commercially available tetanus toxoid, diphtheria, and acellular pertussis (TDaP) vaccine (BOOSTRIX, GlaxoSmithKline plc, Isleworth, London, England). Mice received 25 µl of TDaP diluted in sterile 0.01 M phosphate-buffered saline to a final volume of 100 µl, with or without the anti-IL-4 mAb. For ELISA, 96-well plates were coated with 50 ng/well of tetanus toxoid or unconjugated OVA control in carbonate buffer and blocked with 1% gelatin. Serum from immunized animals was incubated with goat anti-mouse IgG to detect TT-specific IgG antibodies. For $IgG_1$ and $IgG_{2a}$, serum was incubated with anti-mouse $IgG_1$ or $IgG_{2a}$ antibodies (Alpha Diagnostic International, Inc., San Antonio, TX). TT-specific IgG titers were analyzed over time (FIG. 11A) or on day 28 after the first immunization (FIG. 11 B-E). Finally, diphtheria-protecting serum antibodies were analyzed in vitro using a standard diphtheria toxin protection assay using Vero cells as substrate in the laboratory of Dr. Sunil A. David at the University of Minnesota, Department of Medicinal Chemistry. Results are shown in FIG. 11.

Example 11

Male BALB/c mice were immunized with KLH, OXY-KLH, anti-IL-4 mAb, or OXY-KLH plus anti-IL-4 mAb. The OXY-KLH and the unconjugated KLH control were administered subcutaneously on days 0, 14 and 28, while the anti-IL-4 mAb was administered intraperitoneally as in EXAMPLE 2. A week after the third immunization, mice were euthanized with $CO_2$ to perform histopathology and clinical pathology by serum chemistry. Organs were harvested and preserved in 10% formaldehyde (methanol free, ultrapure EM grade, Polysciences, Inc., Warminster, PA), and sent to the University of Minnesota School of Veterinary Medicine for histology analysis in the laboratory of Dr. Davis Seelig. Serum was collected by centrifugation at 7500 rpm for three minutes at 4° C. and collected in lithium heparin (VACUTAINER, Becton, Dickinson and Co., Franklin Lakes, NJ). Frozen samples were sent to Marshfield Labs (Marshfield, WI) for the panel tests analysis.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method comprising:
   co-administering to a subject in need of treatment for opioid drug abuse or toxicity from opioid drug exposure:
   a vaccine comprising an opioid drug conjugated to a carrier polypeptide, wherein the conjugate is effective to induce production of antibody that specifically binds to the opioid drug; and
   an anti-IL-4 antibody, or antigen binding fragment thereof, effective to improve the subject's immune response to the vaccine, wherein the improvement comprises an increase in antigen-specific IgG antibody in the subject, an increase in antigen-specific IgG antibody concentration in the subject, or an increase in antigen-specific IgG antibody titer in the subject compared to the subject's immune response to the vaccine without the anti-IL-4 antibody, or antigen binding fragment thereof.

2. The method of claim 1, wherein the anti-IL-4 antibody, or antigen binding fragment thereof, is complexed with IL-4.

3. The method of claim 1, wherein the anti-IL-4 antibody or an antigen binding fragment thereof, is a monoclonal antibody or a fragment of a monoclonal antibody.

4. A method for producing antibody against a small molecule drug, the method comprising:
   administering to an animal a composition comprising:
   the small molecule drug conjugated to a polypeptide carrier in an amount to induce production of antibody that specifically binds the small molecule drug; and
   an anti-IL-4 antibody, or an antigen binding fragment thereof, in an amount effective to improve the animal's production of antibody against the small molecule drug antigen compared to the animal's production of antibody against the small molecule drug without the anti-IL-4 antibody or antigen binding fragment thereof.

5. The method of claim 4, wherein the anti-IL-4 antibody, or antigen binding fragment thereof, is complexed with IL-4.

6. The method of claim 4, wherein the anti-IL-4 antibody or an antigen binding fragment thereof, is a monoclonal antibody or a fragment of a monoclonal antibody.

* * * * *